United States Patent
Ohtsuka et al.

(10) Patent No.: US 7,695,920 B2
(45) Date of Patent: Apr. 13, 2010

(54) METHODS OF SCREENING COMPOUNDS BINDING TO PRESYNAPTIC PROTEIN CAST

(75) Inventors: Toshihisa Ohtsuka, Kyoto (JP); Etsuko Rikitsu, Aichi (JP); Marie Inoue, Kyoto (JP); Eiji Inoue, Osaka (JP)

(73) Assignee: Eisai R&D Management Co., Ltd, Tokyo (JP)

( * ) Notice: Subject to any disclaimer, the term of this patent is extended or adjusted under 35 U.S.C. 154(b) by 44 days.

(21) Appl. No.: 11/979,099

(22) Filed: Oct. 31, 2007

(65) Prior Publication Data
US 2009/0087842 A1 Apr. 2, 2009

Related U.S. Application Data

(63) Continuation of application No. 10/747,065, filed on Dec. 30, 2003, now Pat. No. 7,297,773, which is a continuation-in-part of application No. PCT/JP03/02718, filed on Mar. 7, 2003.

(30) Foreign Application Priority Data

Mar. 8, 2002 (JP) .............................. 2002-063186

(51) Int. Cl.
  *G01N 33/53* (2006.01)
  *G01N 33/567* (2006.01)
  *G01N 33/566* (2006.01)
  *C07K 1/00* (2006.01)
  *C12P 21/06* (2006.01)

(52) U.S. Cl. ...................... 435/7.1; 435/7.21; 435/7.92; 435/69.1; 436/501; 530/350

(58) Field of Classification Search ........................ None
See application file for complete search history.

(56) References Cited

U.S. PATENT DOCUMENTS

| 7,297,773 B2 | 11/2007 | Ohtsuka et al. |
| 2004/0029790 A1 | 2/2004 | Patturajan et al. |

FOREIGN PATENT DOCUMENTS

| WO | WO 01/75067 A2 | 10/2001 |
| WO | WO 01/75067 A3 | 10/2001 |
| WO | WO 02/070539 A2 | 9/2002 |
| WO | WO 02/070539 A3 | 9/2002 |

OTHER PUBLICATIONS

Database Genesequence Online, Accession No. ABG05140, Drmanac, R.T., et al., Entry Date Feb. 2002.
Database Genesequence Online, Accession No. AAS69327, Drmanac, R.T., et al., Entry Date Feb. 2002.
Ko, J., et al., "Interaction of the ERC Family of RIM-binding Proteins with the Liprin-α Family of Multidomain Proteins," *J. Biol. Chem.* 278:42377-42385, American Society for Biochemistry and Molecular Biology, Inc. (Oct. 2003).
Nagase, T., et al., "Prediction of the Coding Sequences of Unidentified Human Genes. VII. The Complete Sequences of 100 New cDNA Clones from Brain Which Can Code for Large Proteins in vitro," *DNA Res.* 4:141-150, Kazusa DNA Research Institute and Universal Academy Press (1997).
Ohtsuka, T., "Functional Protein-Protein Interactions at the Presynaptic Active Zone," Abstract and Presentation Slides for a RIKEN Brain Science Institute Seminar, KAN Research Institute, pp. 1-11 (Aug. 26, 2002).
Ohtsuka, T., et al., "CAST: a novel protein of the cytomatrix at the active zone of synapses that forms a ternary complex with RIM1 and Munc13-1," *J. Cell. Biol.* 158:577-590, Rockefeller University Press (Aug. 2002).
Okazaki, N., et al., "Prediction of the Coding Sequences of Mouse Homologues of KIAA Gene: II. The Complete Nucleotide Sequences of 400 Mouse KIAA-homologous cDNAs Identified by Screening of Terminal Sequences of cDNA Clones Randomly Sampled from Size-fractionated Libraries," *DNA Res.* 10:35-48, Kazusa DNA Research Institute And Universal Academy Press (Feb. 2003).
Reeck, G.R., et al., "Homology In Proteins and Nucleic Acids: A Terminology Muddle and a Way Out of It," *Cell* 50:667, Cell Press (1987).
Schoch, S., et al., "RIM1α forms a protein scaffold for regulating neurotransmitter release at the active zone," *Nature* 415:321-326, Nature Publishing Group (Jan. 2002).
Wang, Y., et al., "A family of RIM-binding proteins regulated by alternative splicing: Implications for the genesis of synaptic active zones," *Proc. Natl. Acad. Sci. USA* 99:14464-14469, National Academy of Sciences (Oct. 2002).

*Primary Examiner*—Olga N Chernyshev
(74) *Attorney, Agent, or Firm*—Sterne, Kessler, Goldstein & Fox P.L.L.C.

(57) ABSTRACT

The present invention enabled the detection and quantification of CAST, which is localized to synapses and tightly bound to the cytomatrix, and of the mRNA encoding the CAST. Furthermore, it was revealed that CAST functions as a protein scaffold for localizing RIM1 to synapses, contributing as a molecular basis for active zone formation.

2 Claims, 10 Drawing Sheets

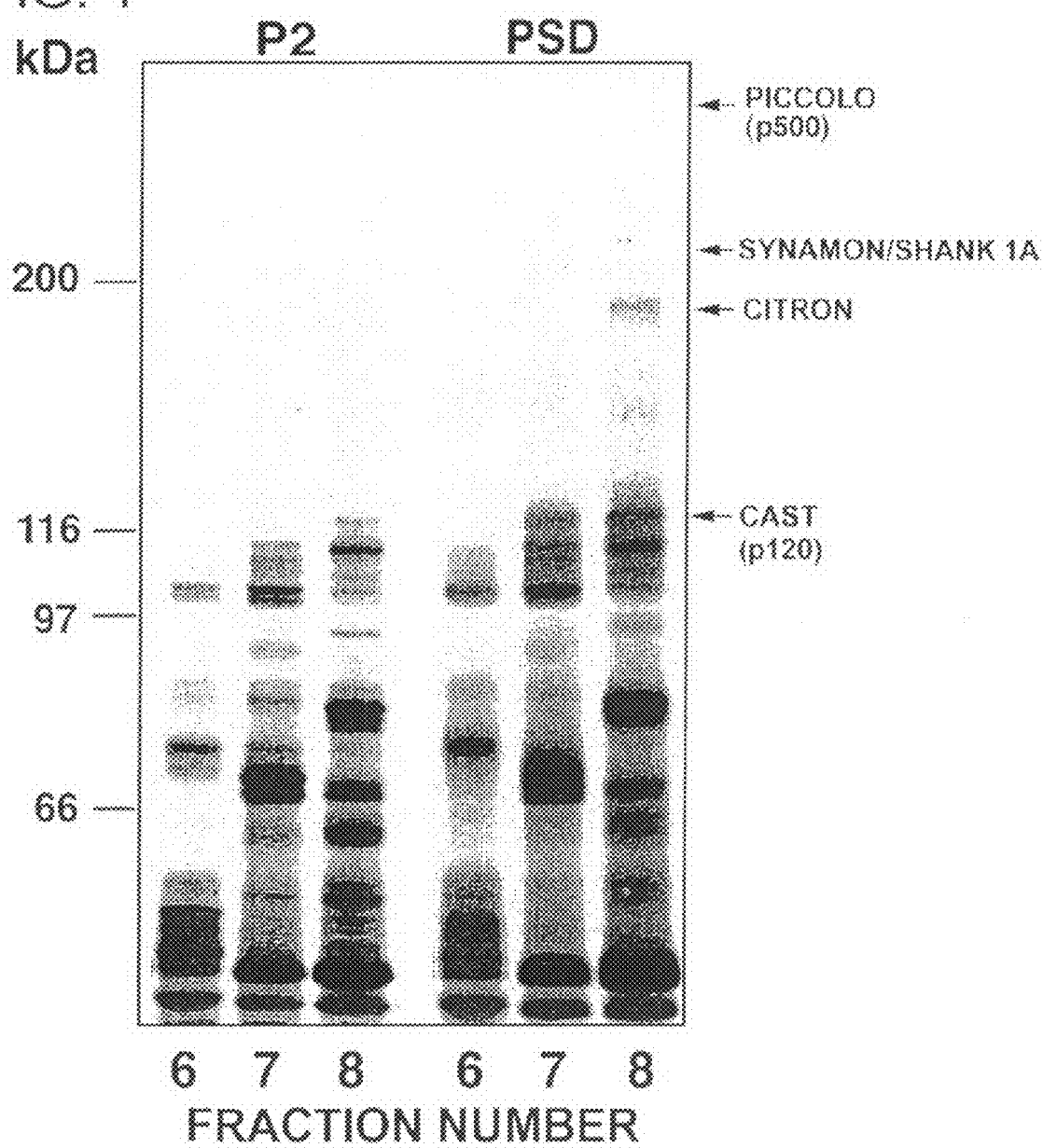

FIG. 2A

```
MYGSARPISN PEGSPSRSPR LPRSPRLGHR RTSSGGGGGT  40
GKTLSMENIQ SLNAAYATSG PMYLSDHEGV ASTTYPKGTM  80
TLGRAINRAV YGGRVTAMGS SPNIASAGLS HIDVLSYTDQ 120
HGGLGGSSHH HHRQVPSMLR QVRDSTMLDL QAQLKELQRE 160
NDLLRKELDI KDSKLGSSMN SIKTFWSPEL KKERVLRKEE 200
AARMSVLKEQ MRVSHEENQH LQLTIQALQD ELRTQRDLNH 240
LLQQESGNRG AEHPTIELTE ENFRRLQAEH DRQAKELFLL 280
RKTLEEMELR IETQKQTLNA RDESIPELLE MLQSKGLPSK 320
SLEDDNEPTR RMAEAESQVS HLEVILDQKE KENIHLREEL 360
HRRSQLQPEP AKTKALQIVI EMKITKIASL ERNIRDLEDE 400
IQMLKANGVL NPEDREEEIK QIEVVKSHSK FMKTENDQLK 440
QELSKKESEL LALQTKLETL SNQNSDCKQH IEVLKBSLTA 480
KEQRAAILQT EVDALRLRLE EKESFLNKRT KQLQDLTEEK 520
GTLAGEIRDM KIMLEVKERK INVLQKKIEN LQBQLRDKDK 560
QLTNLKDRVK SLQTDSSNTD TRLATLEEAL SEKERITERL 600
KEQRERDDRE RLEEIESPRK ENKDLKEKVN ALQAELTEKE 640
SSLIDLKEHA SSLASAGLKR DSKLKSLEIA IEQKKEECNK 680
LRAQLKKAHN IEDDSRMNPE FADRLKQLDK EASYFRDECG 720
KAQAEVDRLL EILKEVENEK NDKIDKKIAEL ESLTLRSMED 760
QNKKVANLKH NQQLEKKKNA QLLEEVRRRE FSMVLNSQHL 800
QIEELMNALE KTRQELDATK ARLASIQQSL AEKEAHLANL 840
RMEREKQLEE ILEMRQEALL AAISEKDANI ALLELSASKK 880
KKTQEEVMAL KREKDRLVHQ LQQYTQNEMK LMADNYDDDH 920
HHYHHHHHH HHRSPGRSQH SNHRPSPDQD DERGIWA    960
```

FIG. 2B

```
kDa
123 —
 83 —
      MOCK  PBS-CAST  NATIVE CAST
```

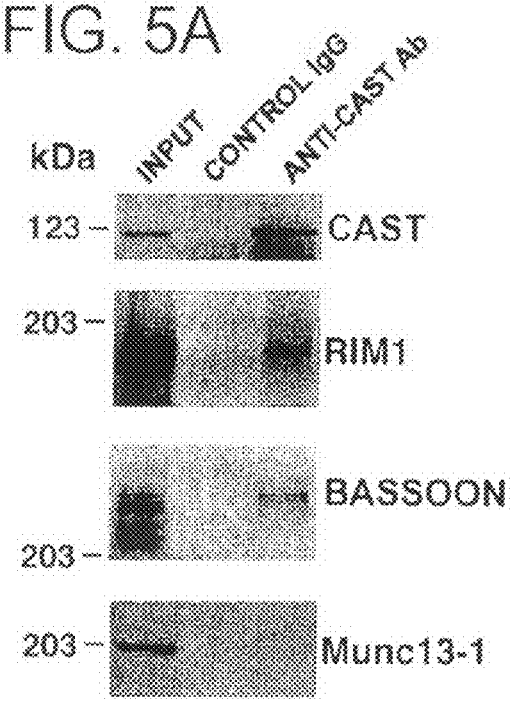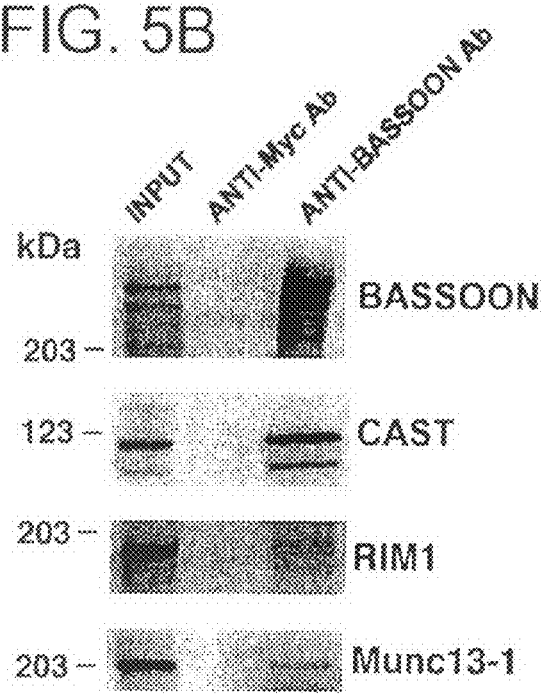

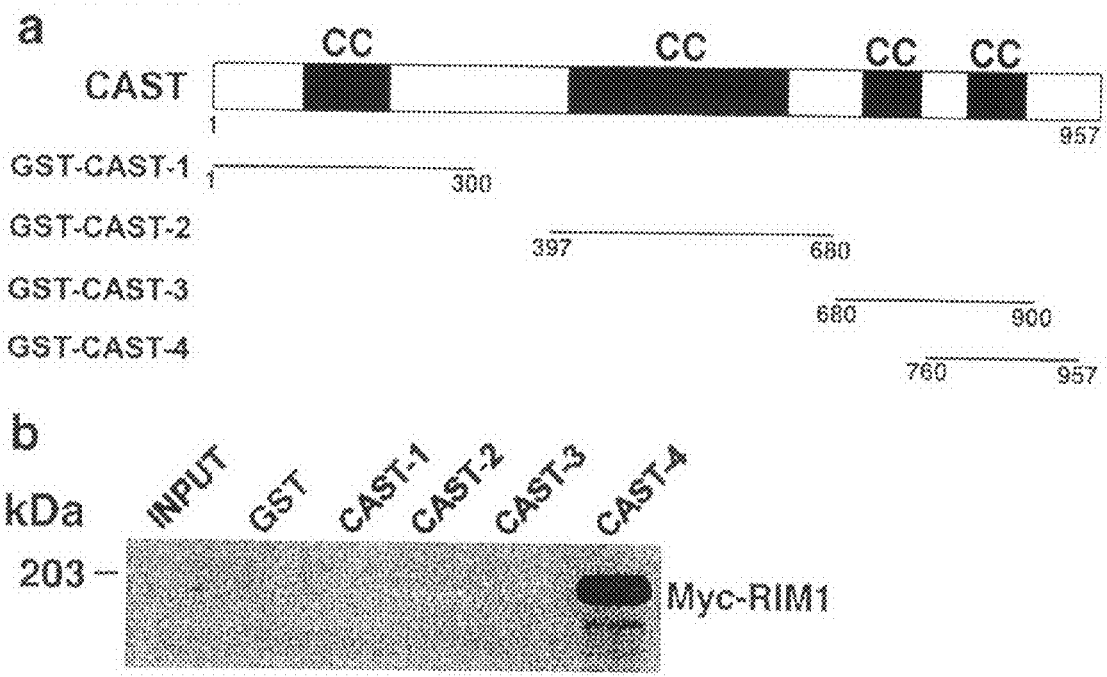

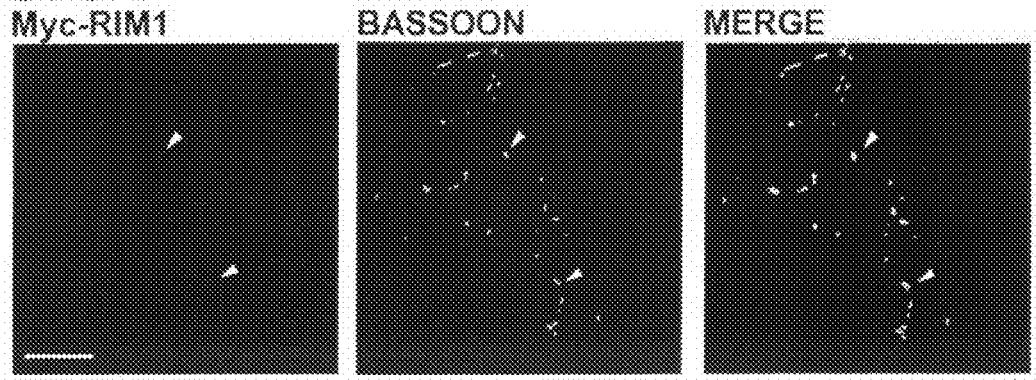
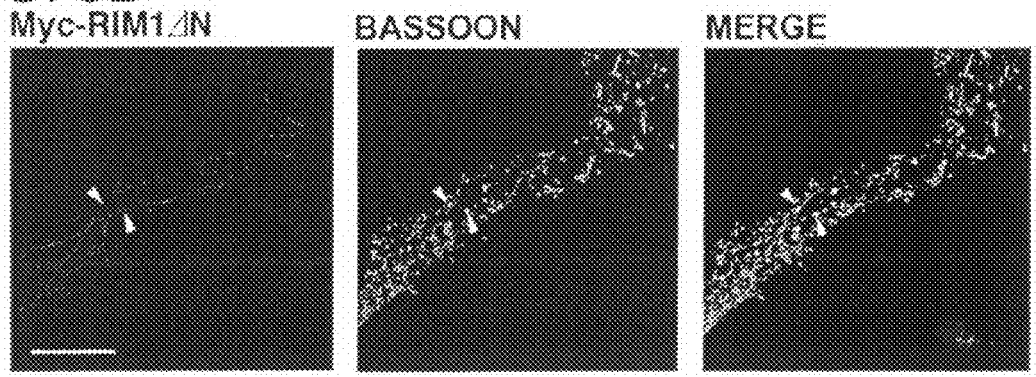
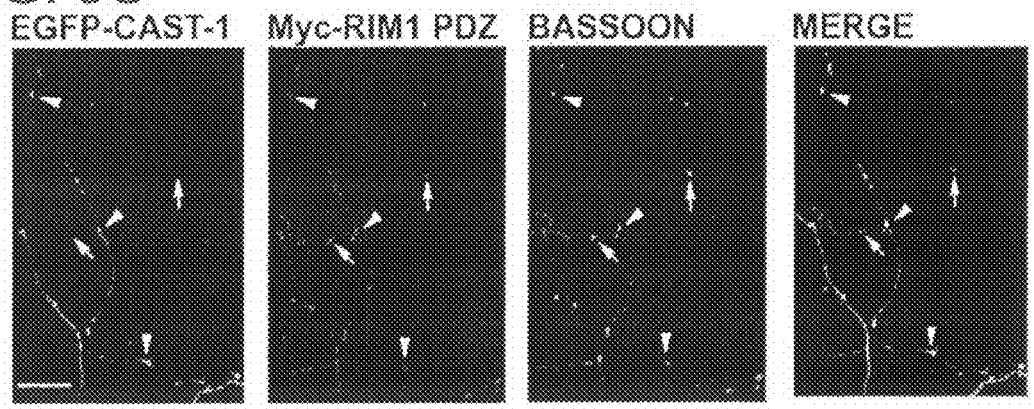

FIG. 10a
```
941              957
SNHRPSPDQDDEEGIWA (SEQ ID NO:5)
    SPDQDDEEGIWA (SEQ ID NO:6)   RID
    SPDQDDEEG    (SEQ ID NO:7)   RIDΔIWA
    ADDQSPEWEIGD (SEQ ID NO:8)   scb RID
```
FIG. 10b
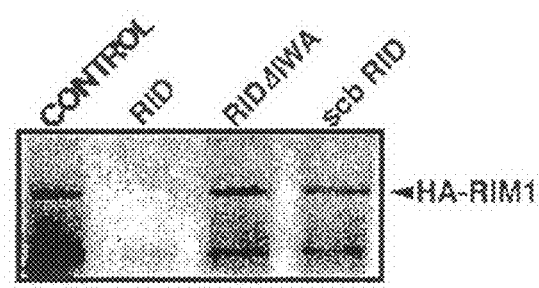
FIG. 10c
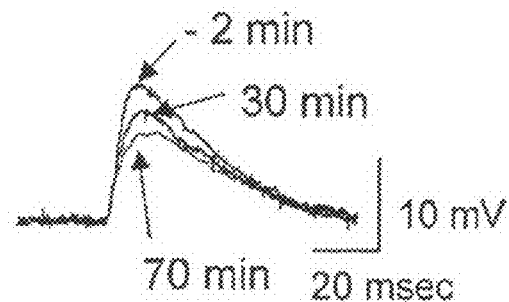
FIG. 10d
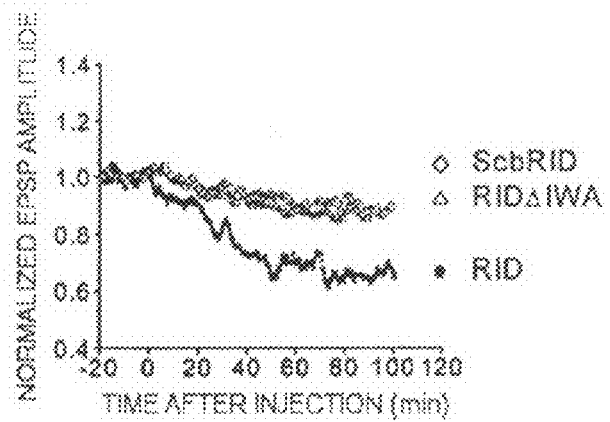

SEQUENCE LISTING

```
<160> NUMBER OF SEQ ID NOS: 8

<210> SEQ ID NO 1
<211> LENGTH: 2932
<212> TYPE: DNA
<213> ORGANISM: Rattus norvegicus
<220> FEATURE:
```

<221> NAME/KEY: CDS
<222> LOCATION: (59)..(2929)

<400> SEQUENCE: 1

```
aagccatcac gctgcctagc atttcttccc ttcagtagcg ccacgtcaca gaagaaaa         58 atg tac ggg agt gca aga aca atc agc aat ccg gaa ggc agc cct tcc        106
Met Tyr Gly Ser Ala Arg Thr Ile Ser Asn Pro Glu Gly Ser Pro Ser
1               5                   10                  15 aga tcg ccg cgt ttg cca agg tct cct cgt ttg ggc cac cga aga aca        154
Arg Ser Pro Arg Leu Pro Arg Ser Pro Arg Leu Gly His Arg Arg Thr
            20                  25                  30 agc agt ggg gga ggg gga ggg aca ggc aag act ctg tct atg gag aac        202
Ser Ser Gly Gly Gly Gly Gly Thr Gly Lys Thr Leu Ser Met Glu Asn
        35                  40                  45 atc cag tcc ctt aat gcg gcc tat gcc acg tct gga ccc atg tac ttg        250
Ile Gln Ser Leu Asn Ala Ala Tyr Ala Thr Ser Gly Pro Met Tyr Leu
50                  55                  60 agt gac cat gaa ggg gtg gca tca aca act tac cca aag ggc acc atg        298
Ser Asp His Glu Gly Val Ala Ser Thr Thr Tyr Pro Lys Gly Thr Met
65                  70                  75                  80 act cta ggc agg gcc aca aat cga gct gtt tat gga ggc cgg gtc aca        346
Thr Leu Gly Arg Ala Thr Asn Arg Ala Val Tyr Gly Gly Arg Val Thr
                85                  90                  95 gcc atg ggg agt agt ccc aat att gct tcc gct gga ctt tcc cac aca        394
Ala Met Gly Ser Ser Pro Asn Ile Ala Ser Ala Gly Leu Ser His Thr
            100                 105                 110 gat gtc ctt tca tat acg gat caa cat gga ggg ctg ggt ggc tca tcc        442
Asp Val Leu Ser Tyr Thr Asp Gln His Gly Gly Leu Gly Gly Ser Ser
        115                 120                 125 cac cac cac cac cac cag gtg ccc tcc atg ttg agg cag gta aga gac        490
His His His His His Gln Val Pro Ser Met Leu Arg Gln Val Arg Asp
130                 135                 140 agc acg atg ttg gat ctt caa gcc cag ctc aaa gaa ctg cag aga gag        538
Ser Thr Met Leu Asp Leu Gln Ala Gln Leu Lys Glu Leu Gln Arg Glu
145                 150                 155                 160 aat gac ctc ctt cgc aag gag ctt gac att aag gac agc aaa ctg ggg        586
Asn Asp Leu Leu Arg Lys Glu Leu Asp Ile Lys Asp Ser Lys Leu Gly
                165                 170                 175 tct tcc atg aat agc atc aag act ttc tgg agt cct gag ctt aag aag        634
Ser Ser Met Asn Ser Ile Lys Thr Phe Trp Ser Pro Glu Leu Lys Lys
            180                 185                 190 gag aga gtc ttg agg aaa gag gag gct gct cgc atg tct gtc ctc aag        682
Glu Arg Val Leu Arg Lys Glu Glu Ala Ala Arg Met Ser Val Leu Lys
        195                 200                 205 gag cag atg agg gtt tct cac gaa gaa aac cag cac ctg cag ttg acc        730
Glu Gln Met Arg Val Ser His Glu Glu Asn Gln His Leu Gln Leu Thr
210                 215                 220 atc cag gcc ctt cag gat gaa ctg cgg acc cag aga gac ctc aac cac        778
Ile Gln Ala Leu Gln Asp Glu Leu Arg Thr Gln Arg Asp Leu Asn His
225                 230                 235                 240 ctc ctg cag caa gag agt ggc aac cga gga gca gag cat ttc acc atc        826
Leu Leu Gln Gln Glu Ser Gly Asn Arg Gly Ala Glu His Phe Thr Ile
                245                 250                 255 gag ctg acg gag gag aac ttc cgc agg ctc caa gcc gaa cac gac agg        874
Glu Leu Thr Glu Glu Asn Phe Arg Arg Leu Gln Ala Glu His Asp Arg
            260                 265                 270 cag gcc aag gag ctg ttc ctt ctg cgg aag aca ttg gaa gaa atg gag        922
Gln Ala Lys Glu Leu Phe Leu Leu Arg Lys Thr Leu Glu Glu Met Glu
        275                 280                 285
```

```
                                                         -continued cta agg att gaa aca cag aaa cag act ctc aat gcc cgc gac gag tcc    970
Leu Arg Ile Glu Thr Gln Lys Gln Thr Leu Asn Ala Arg Asp Glu Ser
    290                 295                 300 att aaa aag ctc ctg gag atg ctg cag agt aag ggc ttg cca tcg aaa   1018
Ile Lys Lys Leu Leu Glu Met Leu Gln Ser Lys Gly Leu Pro Ser Lys
305                 310                 315                 320 agc cta gag gac gac aac gag cgc aca cgg cgg atg gcc gag gct gag   1066
Ser Leu Glu Asp Asp Asn Glu Arg Thr Arg Arg Met Ala Glu Ala Glu
                325                 330                 335 tct cag gtc agc cac ttg gaa gtg att tta gac cag aag gag aag gaa   1114
Ser Gln Val Ser His Leu Glu Val Ile Leu Asp Gln Lys Glu Lys Glu
            340                 345                 350 aac atc cac ctg aga gag gaa ttg cac cga aga agc caa ctt cag ccg   1162
Asn Ile His Leu Arg Glu Glu Leu His Arg Arg Ser Gln Leu Gln Pro
        355                 360                 365 gag cca gcc aag acg aag gcg ctc cag act gtc atc gaa atg aag gac   1210
Glu Pro Ala Lys Thr Lys Ala Leu Gln Thr Val Ile Glu Met Lys Asp
    370                 375                 380 aca aaa att gct tca ctg gag cgg aac atc cgg gac ctc gag gat gag   1258
Thr Lys Ile Ala Ser Leu Glu Arg Asn Ile Arg Asp Leu Glu Asp Glu
385                 390                 395                 400 atc cag atg ttg aaa gcc aat ggt gtg ctc aac aca gag gac cga gag   1306
Ile Gln Met Leu Lys Ala Asn Gly Val Leu Asn Thr Glu Asp Arg Glu
                405                 410                 415 gag gag atc aaa cag atc gag gtg tac aaa agc cac tcc aag ttt atg   1354
Glu Glu Ile Lys Gln Ile Glu Val Tyr Lys Ser His Ser Lys Phe Met
            420                 425                 430 aag acc aag aat gac cag ctg aaa cag gaa ctt tcc aag aag gag tca   1402
Lys Thr Lys Asn Asp Gln Leu Lys Gln Glu Leu Ser Lys Lys Glu Ser
        435                 440                 445 gaa ctt ctt gcc tta caa aca aag ctt gaa acc ctt agc aat cag aat   1450
Glu Leu Leu Ala Leu Gln Thr Lys Leu Glu Thr Leu Ser Asn Gln Asn
    450                 455                 460 tca gat tgc aag caa cac att gaa gtg ctt aaa gag tca ctt act gcc   1498
Ser Asp Cys Lys Gln His Ile Glu Val Leu Lys Glu Ser Leu Thr Ala
465                 470                 475                 480 aaa gaa cag agg gct gcc atc ctt cag act gag gta gat gca ctg aga   1546
Lys Glu Gln Arg Ala Ala Ile Leu Gln Thr Glu Val Asp Ala Leu Arg
                485                 490                 495 tta cgg ctg gaa gag aaa gaa tct ttt ctc aat aag aaa aca aaa cag   1594
Leu Arg Leu Glu Glu Lys Glu Ser Phe Leu Asn Lys Lys Thr Lys Gln
            500                 505                 510 ctc caa gac ctc act gaa gag aag ggg acc cta gct gga gag atc cgt   1642
Leu Gln Asp Leu Thr Glu Glu Lys Gly Thr Leu Ala Gly Glu Ile Arg
        515                 520                 525 gat atg aaa gat atg tta gaa gta aag gaa aga aaa atc aat gtt ctt   1690
Asp Met Lys Asp Met Leu Glu Val Lys Glu Arg Lys Ile Asn Val Leu
    530                 535                 540 cag aaa aaa att gaa aac ttg caa gaa caa ctt agg gat aag gac aaa   1738
Gln Lys Lys Ile Glu Asn Leu Gln Glu Gln Leu Arg Asp Lys Asp Lys
545                 550                 555                 560 caa ctg acc aac ctg aaa gac aga gtg aag tcc ctg cag acg gac tcc   1786
Gln Leu Thr Asn Leu Lys Asp Arg Val Lys Ser Leu Gln Thr Asp Ser
                565                 570                 575 agc aac act gac act gct ctg gcc act ctg gag gag gcc ttg tcg gaa   1834
Ser Asn Thr Asp Thr Ala Leu Ala Thr Leu Glu Glu Ala Leu Ser Glu
            580                 585                 590 aag gag aga ata ata gag cgc ttg aaa gag cag agg gag aga gat gat   1882
Lys Glu Arg Ile Ile Glu Arg Leu Lys Glu Gln Arg Glu Arg Asp Asp
        595                 600                 605
```

```
cgg gaa aga cta gaa gag ata gaa tcc ttt cga aag gag aac aaa gac    1930
Arg Glu Arg Leu Glu Glu Ile Glu Ser Phe Arg Lys Glu Asn Lys Asp
    610                 615                 620 ctc aaa gag aag gtc aat gct tta cag gct gag ctg aca gag aaa gag    1978
Leu Lys Glu Lys Val Asn Ala Leu Gln Ala Glu Leu Thr Glu Lys Glu
625                 630                 635                 640 tct agt tta atc gac ctc aaa gaa cat gca tct tca tta gct tct gca    2026
Ser Ser Leu Ile Asp Leu Lys Glu His Ala Ser Ser Leu Ala Ser Ala
                645                 650                 655 gga ctg aag agg gac tcg aaa cta aag tct cta gaa ata gcc att gaa    2074
Gly Leu Lys Arg Asp Ser Lys Leu Lys Ser Leu Glu Ile Ala Ile Glu
            660                 665                 670 caa aag aag gag gaa tgc aac aaa cta gaa gca caa ttg aaa aag gca    2122
Gln Lys Lys Glu Glu Cys Asn Lys Leu Glu Ala Gln Leu Lys Lys Ala
        675                 680                 685 cat aat att gaa gat gac tcc agg atg aac ccc gag ttt gca gac cga    2170
His Asn Ile Glu Asp Asp Ser Arg Met Asn Pro Glu Phe Ala Asp Arg
    690                 695                 700 ctg aaa cag ctg gac aag gaa gca tct tac tac cgt gat gag tgt ggc    2218
Leu Lys Gln Leu Asp Lys Glu Ala Ser Tyr Tyr Arg Asp Glu Cys Gly
705                 710                 715                 720 aag gct caa gca gaa gtc gac agg ttg ctg gag atc ctc aag gag gtg    2266
Lys Ala Gln Ala Glu Val Asp Arg Leu Leu Glu Ile Leu Lys Glu Val
                725                 730                 735 gag aat gag aaa aac gac aaa gac aag aag att gcg gaa ctt gag agc    2314
Glu Asn Glu Lys Asn Asp Lys Asp Lys Lys Ile Ala Glu Leu Glu Ser
            740                 745                 750 ttg act ctc agg cat atg aaa gat cag aat aag aag gtg gcc aac ctc    2362
Leu Thr Leu Arg His Met Lys Asp Gln Asn Lys Lys Val Ala Asn Leu
        755                 760                 765 aag cac aac caa cag ctg gag aag aag aag aac gcc cag tta tta gaa    2410
Lys His Asn Gln Gln Leu Glu Lys Lys Lys Asn Ala Gln Leu Leu Glu
    770                 775                 780 gaa gtg cgc cgg cga gaa ttt agc atg gtt gac aac tca cag cat ttg    2458
Glu Val Arg Arg Arg Glu Phe Ser Met Val Asp Asn Ser Gln His Leu
785                 790                 795                 800 cag atc gag gag ctg atg aat gcc ttg gag aag acc aga cag gaa ctg    2506
Gln Ile Glu Glu Leu Met Asn Ala Leu Glu Lys Thr Arg Gln Glu Leu
                805                 810                 815 gac gcc acc aaa gca cgc ctc gcc tct acc cag caa tca ttg gct gag    2554
Asp Ala Thr Lys Ala Arg Leu Ala Ser Thr Gln Gln Ser Leu Ala Glu
            820                 825                 830 aag gaa gca cac cta gcc aat ctc cgg atg gag agg agg aaa cag cta    2602
Lys Glu Ala His Leu Ala Asn Leu Arg Met Glu Arg Arg Lys Gln Leu
        835                 840                 845 gag gag atc ttg gag atg aaa cag gaa gcg tta ctt gcg gcc atc agt    2650
Glu Glu Ile Leu Glu Met Lys Gln Glu Ala Leu Leu Ala Ala Ile Ser
    850                 855                 860 gaa aag gat gca aac att gcc ttg ctg gag tta tct gcc tcc aag aag    2698
Glu Lys Asp Ala Asn Ile Ala Leu Leu Glu Leu Ser Ala Ser Lys Lys
865                 870                 875                 880 aaa aag acg cag gag gaa gtc atg gca ctg aag cgg gag aaa gac cga    2746
Lys Lys Thr Gln Glu Glu Val Met Ala Leu Lys Arg Glu Lys Asp Arg
                885                 890                 895 ctg gtg cat cag tta aag cag cag acc cag aat aga atg aag ctg atg    2794
Leu Val His Gln Leu Lys Gln Gln Thr Gln Asn Arg Met Lys Leu Met
            900                 905                 910 gca gac aac tat gac gac gac cac cac cat tac cac cac cac cac cat    2842
Ala Asp Asn Tyr Asp Asp Asp His His His Tyr His His His His His
```

-continued

```
              915                 920                 925
cac cac cac cac cgg tct cct ggg agg tca cag cat tcc aac cac agg      2890
His His His His Arg Ser Pro Gly Arg Ser Gln His Ser Asn His Arg
            930                 935                 940 ccc tct ccg gac cag gat gac gag gag ggc ata tgg gca tag              2932
Pro Ser Pro Asp Gln Asp Asp Glu Glu Gly Ile Trp Ala
945                 950                 955
```

<210> SEQ ID NO 2
<211> LENGTH: 957
<212> TYPE: PRT
<213> ORGANISM: Rattus norvegicus

<400> SEQUENCE: 2

```
Met Tyr Gly Ser Ala Arg Thr Ile Ser Asn Pro Glu Gly Ser Pro Ser
1               5                   10                  15

Arg Ser Pro Arg Leu Pro Arg Ser Pro Arg Leu Gly His Arg Arg Thr
            20                  25                  30

Ser Ser Gly Gly Gly Gly Thr Gly Lys Thr Leu Ser Met Glu Asn
        35                  40                  45

Ile Gln Ser Leu Asn Ala Ala Tyr Ala Thr Ser Gly Pro Met Tyr Leu
50                  55                  60

Ser Asp His Glu Gly Val Ala Ser Thr Thr Tyr Pro Lys Gly Thr Met
65                  70                  75                  80

Thr Leu Gly Arg Ala Thr Asn Arg Ala Val Tyr Gly Gly Arg Val Thr
                85                  90                  95

Ala Met Gly Ser Ser Pro Asn Ile Ala Ser Ala Gly Leu Ser His Thr
            100                 105                 110

Asp Val Leu Ser Tyr Thr Asp Gln His Gly Gly Leu Gly Gly Ser Ser
        115                 120                 125

His His His His His Gln Val Pro Ser Met Leu Arg Gln Val Arg Asp
130                 135                 140

Ser Thr Met Leu Asp Leu Gln Ala Gln Leu Lys Glu Leu Gln Arg Glu
145                 150                 155                 160

Asn Asp Leu Leu Arg Lys Glu Leu Asp Ile Lys Asp Ser Lys Leu Gly
                165                 170                 175

Ser Ser Met Asn Ser Ile Lys Thr Phe Trp Ser Pro Glu Leu Lys Lys
            180                 185                 190

Glu Arg Val Leu Arg Lys Glu Glu Ala Ala Arg Met Ser Val Leu Lys
        195                 200                 205

Glu Gln Met Arg Val Ser His Glu Glu Asn Gln His Leu Gln Leu Thr
210                 215                 220

Ile Gln Ala Leu Gln Asp Glu Leu Arg Thr Gln Arg Asp Leu Asn His
225                 230                 235                 240

Leu Leu Gln Gln Glu Ser Gly Asn Arg Gly Ala Glu His Phe Thr Ile
                245                 250                 255

Glu Leu Thr Glu Glu Asn Phe Arg Arg Leu Gln Ala Glu His Asp Arg
            260                 265                 270

Gln Ala Lys Glu Leu Phe Leu Leu Arg Lys Thr Leu Glu Glu Met Glu
        275                 280                 285

Leu Arg Ile Glu Thr Gln Lys Gln Thr Leu Asn Ala Arg Asp Glu Ser
290                 295                 300

Ile Lys Lys Leu Leu Glu Met Leu Gln Ser Lys Gly Leu Pro Ser Lys
305                 310                 315                 320

Ser Leu Glu Asp Asp Asn Glu Arg Thr Arg Arg Met Ala Glu Ala Glu
```

```
                    325                 330                 335
Ser Gln Val Ser His Leu Glu Val Ile Leu Asp Gln Lys Lys Glu
            340                 345                 350
Asn Ile His Leu Arg Glu Leu His Arg Arg Ser Gln Leu Gln Pro
            355                 360                 365
Glu Pro Ala Lys Thr Lys Ala Leu Gln Thr Val Ile Glu Met Lys Asp
            370                 375                 380
Thr Lys Ile Ala Ser Leu Glu Arg Asn Ile Arg Asp Leu Glu Asp Glu
385                 390                 395                 400
Ile Gln Met Leu Lys Ala Asn Gly Val Leu Asn Thr Glu Asp Arg Glu
            405                 410                 415
Glu Glu Ile Lys Gln Ile Glu Val Tyr Lys Ser His Ser Lys Phe Met
            420                 425                 430
Lys Thr Lys Asn Asp Gln Leu Lys Gln Glu Leu Ser Lys Lys Glu Ser
            435                 440                 445
Glu Leu Leu Ala Leu Gln Thr Lys Leu Glu Thr Leu Ser Asn Gln Asn
            450                 455                 460
Ser Asp Cys Lys Gln His Ile Glu Val Leu Lys Glu Ser Leu Thr Ala
465                 470                 475                 480
Lys Glu Gln Arg Ala Ala Ile Leu Gln Thr Glu Val Asp Ala Leu Arg
            485                 490                 495
Leu Arg Leu Glu Glu Lys Glu Ser Phe Leu Asn Lys Lys Thr Lys Gln
            500                 505                 510
Leu Gln Asp Leu Thr Glu Glu Lys Gly Thr Leu Ala Gly Glu Ile Arg
            515                 520                 525
Asp Met Lys Asp Met Leu Glu Val Lys Glu Arg Lys Ile Asn Val Leu
            530                 535                 540
Gln Lys Lys Ile Glu Asn Leu Gln Glu Gln Leu Arg Asp Lys Asp Lys
545                 550                 555                 560
Gln Leu Thr Asn Leu Lys Asp Arg Val Lys Ser Leu Gln Thr Asp Ser
            565                 570                 575
Ser Asn Thr Asp Thr Ala Leu Ala Thr Leu Glu Glu Ala Leu Ser Glu
            580                 585                 590
Lys Glu Arg Ile Ile Glu Arg Leu Lys Glu Gln Arg Glu Arg Asp Asp
            595                 600                 605
Arg Glu Arg Leu Glu Glu Ile Glu Ser Phe Arg Lys Glu Asn Lys Asp
            610                 615                 620
Leu Lys Glu Lys Val Asn Ala Leu Gln Ala Glu Leu Thr Glu Lys Glu
625                 630                 635                 640
Ser Ser Leu Ile Asp Leu Lys Glu His Ala Ser Ser Leu Ala Ser Ala
            645                 650                 655
Gly Leu Lys Arg Asp Ser Lys Leu Lys Ser Leu Glu Ile Ala Ile Glu
            660                 665                 670
Gln Lys Lys Glu Glu Cys Asn Lys Leu Glu Ala Gln Leu Lys Lys Ala
            675                 680                 685
His Asn Ile Glu Asp Asp Ser Arg Met Asn Pro Glu Phe Ala Asp Arg
            690                 695                 700
Leu Lys Gln Leu Asp Lys Glu Ala Ser Tyr Tyr Arg Asp Glu Cys Gly
705                 710                 715                 720
Lys Ala Gln Ala Glu Val Asp Arg Leu Leu Glu Ile Leu Lys Glu Val
            725                 730                 735
Glu Asn Glu Lys Asn Asp Lys Asp Lys Lys Ile Ala Glu Leu Glu Ser
            740                 745                 750
```

```
Leu Thr Leu Arg His Met Lys Asp Gln Asn Lys Lys Val Ala Asn Leu
        755                 760                 765

Lys His Asn Gln Gln Leu Glu Lys Lys Asn Ala Gln Leu Leu Glu
    770                 775                 780

Glu Val Arg Arg Arg Glu Phe Ser Met Val Asp Asn Ser Gln His Leu
785                 790                 795                 800

Gln Ile Glu Glu Leu Met Asn Ala Leu Glu Lys Thr Arg Gln Glu Leu
                805                 810                 815

Asp Ala Thr Lys Ala Arg Leu Ala Ser Thr Gln Gln Ser Leu Ala Glu
            820                 825                 830

Lys Glu Ala His Leu Ala Asn Leu Arg Met Glu Arg Arg Lys Gln Leu
        835                 840                 845

Glu Glu Ile Leu Glu Met Lys Gln Glu Ala Leu Leu Ala Ala Ile Ser
    850                 855                 860

Glu Lys Asp Ala Asn Ile Ala Leu Leu Glu Leu Ser Ala Ser Lys Lys
865                 870                 875                 880

Lys Lys Thr Gln Glu Glu Val Met Ala Leu Lys Arg Glu Lys Asp Arg
                885                 890                 895

Leu Val His Gln Leu Lys Gln Gln Thr Gln Asn Arg Met Lys Leu Met
            900                 905                 910

Ala Asp Asn Tyr Asp Asp His His His Tyr His His His His
        915                 920                 925

His His His His Arg Ser Pro Gly Arg Ser Gln His Ser Asn His Arg
    930                 935                 940

Pro Ser Pro Asp Gln Asp Asp Glu Glu Gly Ile Trp Ala
945                 950                 955

<210> SEQ ID NO 3
<211> LENGTH: 22
<212> TYPE: DNA
<213> ORGANISM: Artificial
<220> FEATURE:
<223> OTHER INFORMATION: Description of Artificial Sequence: an
      artificially synthesized primer sequence

<400> SEQUENCE: 3
taatggcaga ggctgagtct ca                                              22

<210> SEQ ID NO 4
<211> LENGTH: 23
<212> TYPE: DNA
<213> ORGANISM: Artificial
<220> FEATURE:
<223> OTHER INFORMATION: Description of Artificial Sequence: an
      artificially synthesized primer sequence

<400> SEQUENCE: 4
tcagtcacga atttcaccgg cca                                             23

<210> SEQ ID NO 5
<211> LENGTH: 17
<212> TYPE: PRT
<213> ORGANISM: Artificial
<220> FEATURE:
<223> OTHER INFORMATION: Description of Artificial Sequence: an
      artificially synthesized peptide sequence

<400> SEQUENCE: 5

Ser Asn His Arg Pro Ser Pro Asp Gln Asp Asp Glu Glu Gly Ile Trp
1               5                   10                  15
```

```
Ala

<210> SEQ ID NO 6
<211> LENGTH: 12
<212> TYPE: PRT
<213> ORGANISM: Artificial
<220> FEATURE:
<223> OTHER INFORMATION: Description of Artificial Sequence: an
      artificially synthesized peptide sequence

<400> SEQUENCE: 6

Ser Pro Asp Gln Asp Asp Glu Glu Gly Ile Trp Ala
1               5                   10

<210> SEQ ID NO 7
<211> LENGTH: 9
<212> TYPE: PRT
<213> ORGANISM: Artificial
<220> FEATURE:
<223> OTHER INFORMATION: Description of Artificial Sequence: an
      artificially synthesized peptide sequence

<400> SEQUENCE: 7

Ser Pro Asp Gln Asp Asp Glu Glu Gly
1               5

<210> SEQ ID NO 8
<211> LENGTH: 12
<212> TYPE: PRT
<213> ORGANISM: Artificial
<220> FEATURE:
<223> OTHER INFORMATION: Description of Artificial Sequence: an
      artificially synthesized peptide sequence

<400> SEQUENCE: 8

Ala Asp Asp Gln Ser Pro Glu Trp Glu Ile Gly Asp
1               5                   10
```

US 7,695,920 B2

METHODS OF SCREENING COMPOUNDS BINDING TO PRESYNAPTIC PROTEIN CAST

CROSS REFERENCE TO RELATED APPLICATIONS

This application is a Continuation of U.S. application Ser. No. 10/747,065 filed Dec. 30, 2003 now U.S. Pat. No. 7,297,773, which is a Continuation-in-Part of PCT/JP03/02718, filed on Mar. 7, 2003, which claims priority from Japanese Application No. 2002-063186 filed on Mar. 8, 2002.

FIELD OF THE INVENTION

The present invention relates to a novel protein related to the synaptic cytomatrix and which is useful in the medical field.

BACKGROUND OF THE INVENTION

A great number of neurotransmitter receptors and scaffolding molecules such as PSD-95 are present in the postsynaptic density (PSD) of neural synapses. These molecules play important roles in the formation and structural maintenance of the PSD. Furthermore, cytomatrix proteins such as Bassoon and RIM are present in the cytomatrix that constitutes the presynaptic active zone (i.e., the cytomatrix at the active zone; CAZ). These proteins play crucial roles in the formation and structural maintenance of the active zone. The efficient transmission of signals between synapses is extremely important in learning, and in the construction and maintenance of memories. Hence, it is easy to envision that failure of this process will cause various neuropathic and neurodegenerative disorders.

Numerous molecular groups associated with the molecular mechanism for axonal guidance of neurons (pathfinding) have been identified by analyses using flies and nematodes, enhancing the understanding of the mechanism to a certain extent. However, in subsequent synaptogenesis, much remains to be clarified as to what kind of molecules are temporally and spatially involved in the formation of mature synaptic contacts.

SUMMARY OF THE INVENTION

An objective of this invention is to find a novel protein linked to the cytomatrix and considered to play an important role in synaptogenesis.

In order to identify proteins concentrated at the synaptic junction, the present inventors prepared crude membrane (P2) fractions and PSD fractions from rat cerebrum, and dissolved these in a buffer containing urea. The dissolved samples were then fractionated using an anion exchange column. Each eluted fraction was subjected to electrophoresis and stained, and the band patterns of P2 and PSD fractions were compared. Proteins concentrated in the PSD fraction were identified using these band patterns, and mass spectrometry revealed two proteins (p500 and p120 proteins) that were not found in databases. Hereinafter, the phrase "p120 protein" refers to the protein of this invention and is also described as "CAST".

Amino acid analysis of these proteins revealed that four peptide sequences derived from CAST coincided with the internal sequence of the KIAA0378 protein. The results of further studies showed that the p120 protein is detected mainly in the brain and is tightly bound to the cytomatrix. Furthermore, CAST was also revealed to function as a protein scaffold, localizing to synapses the Rab3A-interacting molecule (RIM1) that plays a critical role in synaptic plasticity (Castillo P. E. et al., Nature 415:327-330, 2002; Schoch S. et al., Nature 415:321-326, 2002).

Specifically, the present invention relates to:

[1] a protein selected from the group consisting of:
 (a) a protein having the amino acid sequence set forth in SEQ ID NO: 2; and
 (b) a protein localized to synapses and having the amino acid sequence set forth in SEQ ID NO: 2, wherein one or more amino acid residues are deleted, substituted, or added;

[2] a DNA encoding the protein of [1];

[3] the DNA of [2] having the nucleotide sequence set forth in SEQ ID NO: 1;

[4] a DNA selected from the group consisting of:
 (a) a DNA having the nucleotide sequence set forth in SEQ ID NO: 1; and
 (b) a DNA that hybridizes under stringent conditions to a DNA that has a nucleotide sequence complementary to the nucleotide sequence set forth in SEQ ID NO: 1, and which encodes a protein localized to synapses;

[5] a DNA selected from the group consisting of:
 (a) a DNA having the nucleotide sequence set forth in SEQ ID NO: 1; and
 (b) a DNA having a nucleotide sequence with 90% or more homology to the nucleotide sequence set forth in SEQ ID NO: 1 and encoding a protein localized to synapses;

[6] a protein encoded by the DNA of [4] or [5];

[7] a recombinant vector comprising the DNA of any one of [2] to [5];

[8] a transformant resulting from transformation of a host with the DNA of any one of [2] to [5];

[9] a method for producing a protein localized to synapses, wherein said method comprises the steps of:
 (1) culturing the transformant of [8]; and
 (2) collecting the protein from the culture, wherein the protein is localized to synapses and expressed by the transformant;

[10] an antibody that reacts with the protein of [1] or [6];

[11] a method for determining the level of the protein of [1] or [6], wherein said method uses the antibody of [10];

[12] a method for measuring the level of a DNA or RNA encoding the protein of [1] or [6], wherein said method uses as a primer or probe an oligonucleotide comprising at least 15 continuous nucleotides of the nucleotide sequence set forth in SEQ ID NO: 1;

[13] a method for detecting the protein of [1] or [6] using the antibody of [10];

[14] a method of screening for a substance that reacts with the protein of [1] or [6], wherein said method comprises the steps of:
 (1) mixing a test substance with the protein of [1] or [6], and produced by the method of [9] or the transformant of [8]; and
 (2) measuring the level of the bound or unbound test substance;

[15] a method of screening for a substance affecting the expression of the protein of [1] or [6], wherein said method comprises the steps of:
 (1) adding a test substance to cells expressing the protein of [1] or [6] followed by culturing; and
 (2) measuring the level of the protein of [1] or [6] which is expressed in the cells, or mRNA encoding said protein;

[16] a method of screening for a substance affecting the expression of the protein of [1] or [6], wherein said method comprises the steps of:

(1) identifying the promoter region controlling the expression of the protein of [1] or [6]; and
(2) measuring the effect of a test substance on the promoter activity;

[17] a method of screening for a substance affecting the distribution of the protein of [1] or [6], wherein said method comprises the steps of:
(1) adding a test substance to cells expressing the protein of [1] or [6] followed by culturing the cells; and
(2) determining the distribution of the protein of [1] or [6];

[18] the protein of [1] that binds to RIM1; and,

[19] an inhibitor for binding of RIM1 to the protein of [1] comprising a peptide selected from the group consisting of:
(1) a peptide comprising the amino acid sequence set forth in SEQ ID NO: 6; and
(2) a peptide comprising the amino acid sequence set forth in SEQ ID NO: 6 wherein one or several amino acids are deleted, substituted, or added.

BRIEF DESCRIPTION OF THE DRAWINGS

FIG. 1 is a photograph showing the electrophoresis band patterns of P2 and PSD fractions eluted using a MonoQ anion exchange chromatography column. CAST was specifically recognized in the PSD fraction.

FIG. 2A represents the coiled-coil domains in the amino acid sequence of CAST; while FIG. 2B is an electrophoretogram showing CAST bands of endogenous CAST, and CAST expressed from CAST cDNA in rabbit reticulocyte extracts. CAST expressed from cDNA showed the same mobility as that of the endogenous CAST.

FIG. 5 is a series of photographs showing (A) CAST, Bassoon, and RIM1, immunoprecipitated by the anti-CAST antibody; and (B) CAST, Bassoon, and RIM1, immunoprecipitated by the anti-Bassoon antibody. CAST co-immunoprecipitated with Bassoon and RIM1, and it was thought that they have a mutual binding activity.

FIG. 6A is a diagram and photograph showing RIM1 co-immunoprecipitated with each domain of CAST; and FIG. 6B is a photograph showing CAST co-immunoprecipitated with each domain of RIM1. The C-terminal domain of CAST was thought to bind to the PSD-95/Discs-Large/ZO-1 (PDZ) domain of RIM1.

FIG. 9 is a series of photographs showing the distribution of fusion proteins of Myc with whole RIM1 (RIM1), RIM1 deprived of the PDZ domain (RIM1ΔN), and RIM1's PDZ domain (RIM1 PDZ). The PDZ domain was required for the distribution of RIM1 into the synaptic active zone.

FIG. 10 shows the involvement of CAST in neurotransmitter release and the effect of CAST peptides on synaptic transmission. (a): The CAST peptide sequences. RID, RIM1-interacting domain; scb RID, scrambled RID. (b): The effect of the peptides (5 mM each) on the binding of HA-RIM1 to immobilized GST-CAST-4. Binding was inhibited by RID but not by RIDΔIWA or scb RID. (c) and (d): The effect of the CAST peptides (1 mM each in the injection) on synaptic transmission. The presynaptic neuron was stimulated every 20 seconds. The CAST peptides were introduced into the presynaptic neuron at t=0. EPSPs from the representative experiments with the injection are illustrated in (c). Normalized and averaged EPSP amplitudes are plotted from five experiments with RID (●), RIDΔIWA (Δ), or scb RID peptide (◇) in (d).

DETAILED DESCRIPTION OF THE INVENTION

Figure 3A:
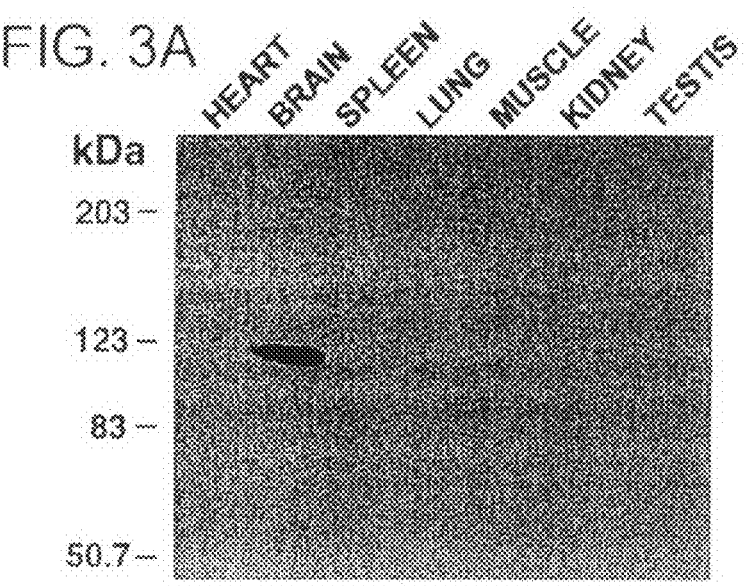
FIG. 3 is a set of photographs showing (A) the organ distribution of CAST; (B) the distribution of CAST in each cellular fraction; and (C) the solubilization of CAST by non-ionic and ionic surfactants. CAST was thought to be distributed in synapses and tightly linked to the cytomatrix.

The present invention is specifically described as follows.

Among the proteins of this invention, the protein comprising the amino acid sequence described in SEQ ID NO: 2 has been identified as a protein localized in synapses, as described in the Examples below. In the field of neuroscience, when, for example, the presence of a protein in synapses is to be proven, a protein whose presence in synapses has already been established as a synaptic marker is generally used. Furthermore, structural alterations of synapses are known to be associated with diseases (Purpura, D. P., Dendritic spine "dysgenesis" and mental retardation, Science 186: 1126-1128, 1974; Geinisman Y., de Toledo-Morrell L., Morrell F., Persina I. S., and Rossi M., Age-related loss of axospinous synapses formed by two afferent systems in the rat dentate gyrus as revealed by the unbiased stereological dissector technique, Hippocampus 2: 437-444 (1992). Therefore, it is thought that the proteins of this invention, and the DNA encoding these proteins, will be useful as synaptic markers in research and diagnostic fields. Furthermore, when the above-described structural alterations in synapses are due to mutation and deletion of CAST, proteins of this invention and DNAs encoding these proteins can also be applied to the treatment for disorders caused by structural alterations in synapses.

In addition, one aspect of proteins of this invention relates to the function of interaction with active zone proteins of synapses, such as RIM1 and Bassoon. Proteins of this invention in particular are capable of binding to RIM1 at the C terminus thereof, so as to localize RIM1 to synapses. Therefore, proteins of this invention and DNAs encoding these proteins may be used in the fields of research and medicine for localizing RIM1 to synapses.

It can be presumed that proteins have functionally identical mutants. Such mutants can be obtained by appropriate modification of the amino acid sequences of the original proteins. Therefore, the proteins of this invention also include proteins that are localized to synapses and which comprise the SEQ ID NO: 2 amino acid sequence in which one or more amino acids have been deleted, substituted, or added.

An amino acid substitution is preferably one in which the properties of the amino acid side-chain are conserved. A "conservative amino acid substitution" is a replacement of one amino acid residue belonging to one of the following groups having a chemically similar side chain with another amino acid in the same group. Groups of amino acid residues having similar side chains have been defined in the art. These groups include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The number of amino acids that may be mutated is not particularly restricted, so long as the activity of the protein of this invention is maintained. Generally, up to about 50 amino acids may be mutated, preferably up to about 30 amino acids, more preferably up to about 10 amino acids, and even more preferably up to about 3 amino acids. Likewise, the site of mutation is not particularly restricted, so long as the mutation does not result in the disruption of the activity of the protein of the present invention.

Protein amino acid sequences can be modified using known techniques, such as site-specific mutagenesis, to modify the DNA nucleotide sequences encoding the proteins, and then expressing the DNA containing the modified nucleotide sequences. One skilled in the art can confirm the localization of a protein to synapses by using fluorescent antibody methods.

When the above-described mutant of the protein that is functionally identical to the protein as a synaptic marker, it is enough that the mutant is able to maintain at least the property to be localized to synapses as described above. On the other hand, when the mutant that is functionally identical to the protein is used for the interaction with RIM1, Bassoon and the like, it is necessary to select the mutant which is capable of interacting with RIM1, Bassoon, etc. One skilled in the art can easily select such mutants capable of interacting with RIM1, Bassoon and the like, and, more specifically, the selection can be performed with reference to Example 5.

Localization can also be confirmed using a fusion protein formed by fusing a protein of this invention with glutathione transferase (GST), His tag, or Green Fluorescent Protein (GFP).

As used herein, a "DNA" is an isolated nucleotide sequence the structure of which is not identical to that of any naturally occurring nucleic acid or to that of any fragment of a naturally occurring genomic nucleic acid spanning more than three genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in random, uncharacterized mixtures of different DNA molecules, transfected cells, or cell clones, e.g., as these occur in a DNA library such as a cDNA or genomic DNA library.

The DNAs of the present invention encode the proteins of this invention and include the DNA that comprises the nucleotide sequence set forth in SEQ ID NO: 1. This DNA has been sequenced according to the Example described below. Genes of the present invention are predicted to include genes which encode identical products but which differ in their nucleotide sequences, and genes that encode mutants with identical functions. By modifying the nucleotide sequences it is also possible to obtain genes that encode mutants encoding identical products or have identical functions. Therefore, the DNAs of this invention also include DNAs that have nucleotide sequences similar to that of SEQ ID NO: 1, that encode proteins localized to synapses, and that encode proteins capable of binding to RIM or Bassoon. Such DNAs can be derived from humans, rats, mice, nematodes, and the like, however, are not limited to these sources. Nematodes in particular are extremely useful as model organisms for studying the nervous system. In fact, the presence of a protein of this invention in nematodes has already been proven (Ohtsuka T. et al., J Cell Biol. 158 (3):577-90 (2002).

In this invention, "DNA having a similar nucleotide sequence" includes DNAs that hybridize under stringent conditions to a DNA comprising a nucleotide sequence complementary to that set forth in SEQ ID NO: 1, or DNAs that are homologous to the nucleotide sequences set forth in SEQ ID NO: 1 or NO: 3, such that the nucleotide sequence is 90% or more, preferably 95% or more, more preferably 98% or more, and even more preferably 99% or more homologous.

Herein, stringent conditions refer to, for example, hybridization in 4×SSC at 65° C. followed by washing in 0.1×SSC at 65° C. for one hour. Alternative stringent conditions are hybridization in 50% formamide followed by washing in 4×SSC at 42° C. In addition, alternative conditions are hybridization in PerfectHyb™ (TOYOBO) solution at 65° C. for two and a half hours followed by washing 1) in 2×SSC and 0.05% SDS at 25° C. for five minutes, 2) in 2×SSC and 0.05% SDS at 25° C. for 15 minutes, and 3) in 0.1×SSC and 0.1% SDS at 50° C. for 20 minutes (highly stringent conditions).

Homology as described herein is homology as calculated by the ClustalW method.

A portion of a DNA of this invention can be utilized as a primer or probe to analyze a gene which encodes CAST, and the expression of this gene. Furthermore, a portion of a DNA of this invention can be used as a primer or probe in the detection of synapses. Thus, a DNA of this invention can be used in a reagent or kit for use in synapse-detecting research or diagnosis. In addition to a DNA of this invention, the kit of the present invention may contain a DNA encoding a peptide fragment of CAST. Such CAST peptide fragments include fragments capable of inhibiting the binding of CAST to RIM1. For example, a fragment at the C-terminus of CAST which comprises approximately ten amino acids including the three amino acids (IWA) necessary for binding between CAST and RIM1 could be such a fragment. The fragment RID (set forth in SEQ ID: 6) as shown in the Examples below is preferable. However, such fragments are not limited to this example. For example, the fragment capable of inhibiting the binding of CAST to RIM1 also includes a fragment comprising the amino acid sequence set forth in SEQ ID NO: 6 wherein one or several amino acids are deleted, substituted, or added, and having the activity to inhibit the binding of CAST with RIM1.

In this invention, "a portion of DNA" refers to an oligonucleotide used as a primer or probe and which comprises at least ten polynucleotides corresponding to DNA sequences of this invention. Such polynucleotides comprise preferably at least 15 nucleotides, and more preferably at least about 20 to 30 nucleotides. Furthermore, polynucleotides comprising larger macromolecules and full-length DNAs can also be used as probes.

The DNA of this invention can be obtained using standard methods based on identified nucleotide sequences. For example, the DNA can be chemically synthesized. Alternatively, it can be obtained by using appropriately prepared primers and RT-PCR or mRNA prepared from neurons and brain tissues.

Gene manipulation can be carried out according to the method described in the reference: Maniatis et al., Molecular Cloning: A Laboratory Manual, Cold Spring Harbor Laboratory, 1989.

There is no particular limitation as to the vectors of this invention so long as they are capable of stably maintaining the inserted DNA. For example, when *E. coli* is used as a host, pBluescript vector (Stratagene) or a similar vector is preferable as a cloning vector. When using a vector in the production of a protein of this invention, expression vectors are particularly useful. There are no particular limitations as to the specific type of expression vector, so long as it is capable of expressing the protein in vitro, in *E. coli*, in cultured cells, and in living organisms. However, for example, the pBEST vector (Promega) is preferable for in vitro expression; pET vector (Invitrogen) is preferable for *E. coli* expression; pME18S-FL3 vector (GenBank Accession No. AB009864) is preferable for expression in cultured cells; and pME18S vector (Takebe Y. et al., Mol Cell Biol. 8:466-472, 1988) is preferable for expression in living organisms. The DNA of this invention can be inserted into the vector using standard methods like the ligase reaction using restriction enzyme sites (Current Protocols in Molecular Biology edit. Ausubel et al. (1987). John Wiley & Sons, Section 11.4-11.11.

Transformants of the present invention can be obtained by transforming hosts with a DNA of this invention, thereby expressing a protein of this invention. A vector of the present invention can be introduced into various hosts without particular limitation, and a specific host can be selected in accordance with the objectives. Examples of hosts used for protein expression include bacterial cells (e.g., *Streptococcus, Staphylococcus, E. coli, Bacillus subtilis*), fungus cells (e.g., yeast, *Streptomyces, Aspergillus*), insect cells (e.g., *Drosophila* S2, *Spodoptera* SF9), animal cells (e.g., CHO, COS, HeLa, C127, 3T3, BHK, HEK293, Bowes melanoma cells), and plant cells. Introduction of a vector into host cells can be performed using a known method such as calcium phosphate precipitation, electroporation (Current Protocols in Molecular Biology edit., Ausubel et al. (1987). John Wiley & Sons, Section 9.1-9.9), lipofectamine (GIBCO-BRL) method, and microinjection.

The methods of production of the present invention are methods for producing proteins of the present invention that are localized to synapses. The methods include culturing transformants of the present invention, and collecting from the culture proteins which are localized to synapses and expressed by the transformants.

The transformants may be cultured under conditions that enable the expression of a protein of the present invention. The protein can be recovered from the culture by appropriately combining routine methods for protein purification, such as various types of chromatography, electrophoresis, and gel filtration. When the proteins of this invention are expressed as fusion proteins with GST or His tag, they can be purified using glutathione-Sepharose or nickel-Sepharose columns, respectively. Purified proteins can be used, for example, for antibody production.

Antibodies can be produced by using the whole CAST of the present invention, or a part thereof, as an epitope. The resulting antibodies can be used by one skilled in the art to detect synapses by known methods. For example, the method described in Example 4 could be employed to detect synapses. Therefore, the antibody of the present invention can be used in a reagent or kit for use in synapse-detecting research or diagnosis. The kit of this invention may comprise a CAST peptide fragment in addition to an antibody of this invention.

In this invention, the term "epitope" means a polypeptide's antigenic determinant, generally comprising at least six amino acids. It is well known in the art that polypeptides consisting of six amino acids can bind with antibodies (Published Japanese Translation of International Publication No. Sho 60-500684). Antigenic peptides of the present proteins mean polypeptides which comprise at least six, preferably at least eight, more preferably at least about 15, and furthermore preferably at least about 20 continuous amino acids based on the amino acid sequences of the proteins of the present invention.

An Antibody of the present invention can be obtained from animals that have been immunized with a protein of the present invention and prepared by a production method of the present invention. Polyclonal antibodies are prepared from sera of the immunized animals described above. Monoclonal antibodies are prepared by fusing myeloma cells with antibody-producing cells obtained from the spleen or lymph nodes of the aforementioned immunized animals, and then selecting hybridomas that produce an antibody to the protein of the present invention with a high specificity.

A protein of the present invention, which is obtained by a method of production of the present invention, can be used as an immunogen. Alternatively, the immunogen may be a fragment or a peptide comprising a partial structure appropriately selected from the amino acid sequence set forth in SEQ ID NO: 2. A variety of condensing agents, such as glutaraldehyde-, carbodiimide-, or maleiimide-activated esters can be used to prepare an antigen-carrier protein complex. Commonly-used carrier proteins such as bovine serum albumin, thyroglobulin, and hemocyanin may be used in the coupling reaction, generally in one- to five-fold excess over the antigen.

The animals to be immunized include mice, rats, rabbits, guinea pigs, hamsters, etc. The animals are inoculated with the antigen subcutaneously, intramuscularly, or intraperitoneally. Prior to administration, the antigen may be mixed with complete Freund's adjuvant or incomplete Freund's adjuvant, and administered usually once every two to five weeks. Antibody-producing cells obtained from the spleens or lymph nodes of immunized animals are fused with myeloma cells and isolated as hybridomas. The myeloma cells used are derived from mice, rats, humans, etc. The myeloma cells are preferably obtained from the same species as that providing the antibody-producing cells; however, it is also possible to use different species.

Cell fusion can be carried out, for example, according to the method of Köhler and Milstein (Nature, 256, 495-497, 1975). Polyethylene glycol, Sendai virus, and so on can be used as fusion accelerators. However, cell fusion is usually carried out using polyethylene glycol (average molecular weight: 1,000 to 4,000) at a concentration of about 20% to 50%, at 20° C. to 40° C., and preferably at 30° C. to 37° C. The ratio of antibody-producing cells to myeloma cells is generally from 1:1 to 10:1.

Various immunochemical methods can be used in screening for antibody-producing hybridomas. For example, Enzyme-linked immunosorbent assays (ELISAs) in which microtiter plates are coated with a protein of this invention; enzyme immunoassays (EIAs) in which microtiter plates are coated with anti-immunoglobulin antibodies; immunoblotting using a nitrocellulose transfer membrane following electrophoresis of samples containing a protein of this invention, etc.

Hybridoma clones are obtained by cloning samples in the wells of such microtiter plates. This may be carried out by, for example, a limiting dilution assay. The hybridomas are screened and cultured, usually in a medium for animal cells (e.g., RPMI1640) that contains 10% to 20% fetal bovine serum supplemented with hypoxanthine, aminopterin, and thymidine (HAT). Clones thus obtained are introduced into the peritoneal cavity of mice, preferably SCID mice, pre-administered with pristane. Ascites containing the monoclonal antibody in high concentrations are harvested ten to 14 days later and can be used as raw materials for antibody purification. Alternatively, the clones are cultured, and the resulting culture can be used as material for antibody purification. Collection of monoclonal antibodies for immunoglobulin purification may be easily performed using known methods such as ammonium sulfate fractionation, PEG fractionation, ethanol fractionation, anion exchange, and affinity chromatography.

Qualitative and quantitative analyses of a protein of the present invention can be conducted in vivo by an immunological method using a monoclonal antibody obtained by the present invention. Known immunological methods (such as immunohistochemical staining, EIA, aggregation, competitive assays, or the sandwich method) can be applied to biological samples which have been suitably treated as necessary, for example, samples subjected to cell isolation or extraction. Immunohistochemical staining can be carried out, for example, by directly using labeled antibodies, or by indirect methods using labeled antibodies against that antibody. Any known labeling substances, such as fluorescent substances, radioactive substances, enzymes, metals, and dyes can be used.

A monoclonal antibody of this invention can be a Fab' or Fab fraction deprived of the Fc' or Fc region, respectively, or it may be an aggregate of these fractions. The monoclonal antibody may also be a chimeric antibody or a humanized antibody.

Pharmaceuticals that influence the expression of a protein of the present invention can be screened as described below:

A cell strain that expresses a protein of the present invention is selected by Northern blotting, RT-PCR, etc. Selection may also be carried out by using an antibody obtained by the above-described method in fluorescent antibody assays, enzyme immunoassays, etc.

A selected cell strain is cultured in the presence of a test pharmaceutical. The effect of this test pharmaceutical on the expression of a protein of the present invention is determined by quantifying the level of mRNA expression (using Northern blotting, slot blot hybridization, RT-PCR, etc.), or by quantifying the level of protein expression (using fluorescent antibody assays, enzyme immunoassays, etc.).

Furthermore, a wide variety of pharmaceuticals may be screened more easily if the following method is used. Specifically, cDNA clones capable of hybridizing to the 5' region of cDNA for a protein of the present invention are selected from a human DNA library. These clones are then inserted into an appropriate promoter screening system and clones with promoter activity are selected. Depending on the situation, the DNA region essential for the promoter activity may be narrowed at this stage.

DNA comprising a promoter region of a protein of the present invention is thus selected. A reporter gene is then constructed by inserting this DNA upstream of DNA encoding enzymes whose activity can be easily assayed, such as luciferase or alkaline phosphatase. The resulting reporter gene is transduced, together with appropriate resistance genes such as Neo$^r$ and Hyg$^r$, into cells that can be cultured, such as HeLa cells. Cells are then selected using pharmaceuticals that correspond to particular resistance genes. Thus, it is possible to establish a cell strain that can be used to assay the activity of a promoter that expresses a protein of the present invention. The activity of the transduced enzyme in this cell strain is measured in the presence of a pharmaceutical. Hence pharmaceuticals that affect the expression of a protein of the present invention can be screened.

As an alternative screening system, compounds that affect the intracellular localization of a protein of the present invention may be selected. In one example of a screening method, an antibody obtained by the above-described method is used to stain (using staining methods such as fluorescence antibody assays, enzyme immunoassays, etc.) a cell strain that expresses a protein of the present invention, or a transformant thereof, and through microscopic observation, measuring the influence of a test pharmaceutical on the intracellular localization of a protein of the present invention. For example, this screening can be performed according to the method of Examples 3 and 6.

Furthermore, in an alternative screening system, compounds that bind to a protein of the present invention can be selected. Compounds binding to a protein of the present invention are likely to affect the protein's function. Equally, and as shown in the Examples, the protein of the present invention shows exocrine gland specificity in its distribution. Thus, if a compound is able to bind specifically to a protein of the present invention, it may express organ-specific actions. Furthermore, compounds binding to a protein of the present invention can be used in synapse detection. For example, synapses can be detected by administering the labeled compound to, or bringing it into contact with, test subjects. Thus, the present invention also provides a method of screening for reagents for synapse-detecting research or diagnosis. One example of a screening method uses a transformant of the present invention, a transformant's cytomatrix, an isolated protein of the present invention or a partial peptide thereof, etc. In this method, a protein of the present invention is reacted with a test compound under appropriate conditions. The presence or absence of a bond between the two is then detected. Bonds can be detected by, for example, appropriate use of labeled substances.

Furthermore, in another alternative screening system, compounds that inhibit binding of a protein of the present invention to RIM1 can be selected. As an example of such a compound, a peptide comprising the amino acid sequence set forth in SEQ ID NO: 6 is mentioned. Compounds that inhibit binding of a protein of the present invention to RIM1 can be used for reducing a release of neurotransmitter such as acetylcholine and inhibiting synaptic transmission, as is shown in Example 6.

CAST structurally analyzed in the present invention is rat-derived. However, when human-derived CAST is used, the methods of the present invention entailing the analysis and screening of the CAST gene are also included in the scope of the present invention.

The present invention enables the detection and quantification of CAST and of mRNA encoding CAST. CAST is localized to synapses and tightly bound to the cytomatrix. Furthermore, it was revealed that p120 functions as a protein scaffold for the localization of RIM1 to synapses, contributing on a molecular basis to the formation of the active zone. The present invention also provides markers, probes, and antibodies that can be used in synapse detection. Furthermore, the present invention provides methods of screening for compounds that can be used in synapse detection.

All patents, published patent applications, and publications cited herein are incorporated by reference in their entirety.

BEST MODE FOR CARRYING OUT THE INVENTION

The present invention will be specifically described with reference to Examples below; however, it is not to be construed as being limited thereto.

Example 1

Cloning of DNA Encoding CAST

To identify proteins concentrated in the synaptic junction, crude membrane (P2) and PSD fractions were prepared from rat cerebrum using sucrose density-gradient centrifugation (Cohen et al., J. Cell Biol. 74:181-203, 1977). Each fraction was dissolved in a urea-containing buffer. These dissolved samples were then separately fractionated on Mono Q anion exchange chromatography columns (Pharmacia). Following electrophoresis, each eluted P2 and PSD fraction was stained and band patterns were compared to identify 20 proteins concentrated in the PSD fraction. Some of these bands are shown in FIG. 1.

Mass spectrometry showed that most of these 20 proteins were identical to proteins whose localization in synapses had been already reported. peptide sequences were identical to the internal sequence of the KIAA0378 protein. Further analysis of the protein was performed since little is known about the function of the KIAA0378 protein, in spite of the registration of its partial amino acid sequence. Herein, this p120 protein is referred to as "CAST".

Based on the cDNA of the registered KIAA0378 (as described in Kikuno, R., Nagase, T., Waki, M. & Ohara, O. (2002) HUGE: a database for human large proteins identified in the Kazusa cDNA sequencing project. Nucleic Acids Res. 30, 166-168), primers set forth in SEQ ID NOs: 3 and 4 were designed and probes were prepared using PCR. Using this probe, a rat hippocampus cDNA library was screened to obtain no less than ten clones. Of these, the two clones with the longest sequences were linked to form the full-length cDNA. This nucleotide sequence is set forth in SEQ ID NO: 1. Its deduced amino acid sequence is set forth in SEQ ID NO: 2 (illustrated in FIG. 2A).

The protein encoded by the full-length cDNA consists of 957 amino acid residues with a few coiled-coil domains (FIG. 2A). The protein did not have any acknowledged domain structures in particular. However it did have a repetitive histidine sequence in its C-terminal region. In order to confirm that the cloned cDNA actually encoded the full-length amino acid sequence of the originally purified CAST, the cDNA was incorporated into an expression vector, and mRNA was then extracted to express the protein in rabbit reticulocyte extracts (Promega). The antibody prepared in Example 2 also reacted with the endogenous CAST, and electrophoresis showed that the protein encoded by the cDNA and the endogenous CAST had almost the same mobility (FIG. 2B). Therefore, it was concluded that this cDNA encodes the full-length amino acid sequence of CAST.

Example 2

Preparation of an Antibody to Cast

A rabbit polyclonal antibody to CAST was prepared as follows: The gene encoding the fusion protein of glutathione S-transferase (GST) and amino acids 180 to 380 of SEQ ID NO: 2 was incorporated into an expression vector. The transformed vector was introduced into E. coli (JM109) and the fusion protein thus expressed purified using a glutathione-Sepharose column. Rabbits were then immunized with this purified protein.

Example 3

Biochemical Examination of CAST Distribution

First, the CAST distribution in each organ was examined. Rats were infused with a PBS solution containing a protease inhibitor, and then their various organs were removed. Homogenates were prepared by disintegrating each organ with a Teflon or polytron homogenizer. After the quantification of proteins, 20 μg of each of the homogenates was electrophoresed, transferred onto a nitrocellulose membrane, and subjected to Western blotting using the above-described anti-CAST antibody. A band of approximately 120 kDa in MW was detected in the brain homogenates (FIG. 3A). No band was detected in heart, spleen, lung, skeletal muscle, kidney, and testis, indicating that CAST is specifically expressed in the brain.

Figure 3B:
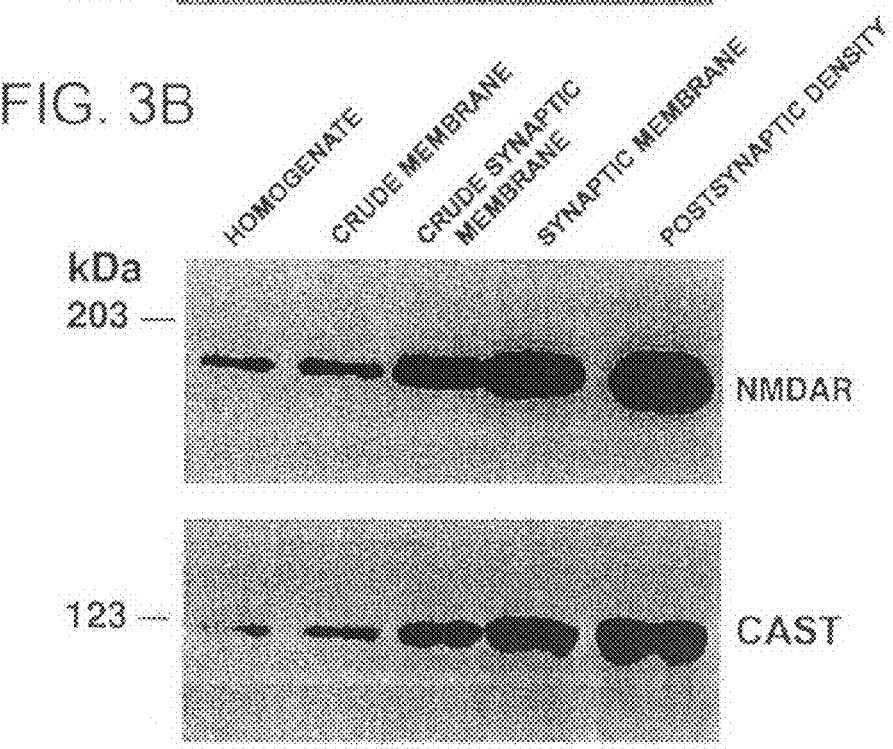

Intracellular localization of p120 protein in the brain was then examined. After electrophoresis of membrane fractions separated by subcellular fractionation (Cohen et al., J. Cell Biol. 74:181-203, 1977), Western blotting was performed using the anti-CAST antibody. Both CAST and the NMDA receptor control were concentrated in the PSD fraction (FIG. 3B).

Figure 3C:
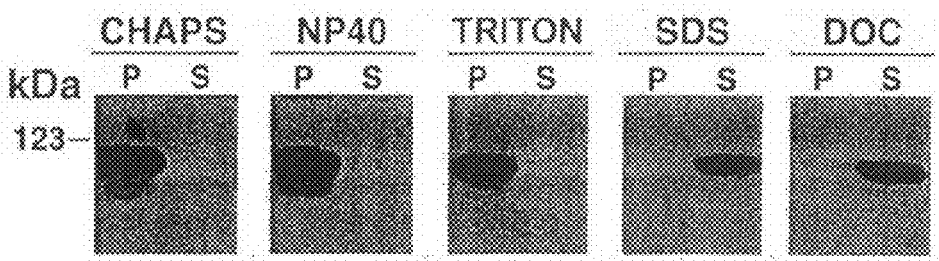

CAST was solubilized using a variety of surfactants. P2 fractions were treated with CHAPS, NP40, Triton X-100, SDS, or DOC at room temperature for 30 minutes. Each sample was then ultracentrifuged (at 100,000×g) and separated into supernatant and precipitate. Equivalent amounts of supernatant and precipitate were electrophoresed, and then subjected to Western blotting using the anti-CAST antibody. CAST was not solubilized in non-ionic surfactants such as CHAPS, NP40, and Triton X-100, and was recovered in the precipitate (FIG. 3C). However, the p120 protein was solubilized by ionic surfactants, SDS and DOC, and thus recovered in the supernatant. These results indicate that CAST is localized to the synaptic junction and tightly bound to the cytomatrix.

Example 4

Tissue Distribution of CAST

Since the above-described biochemical data suggested that CAST is a synaptic protein, p120 protein localization to the synapses in actual tissues was examined.

Figure 4A:
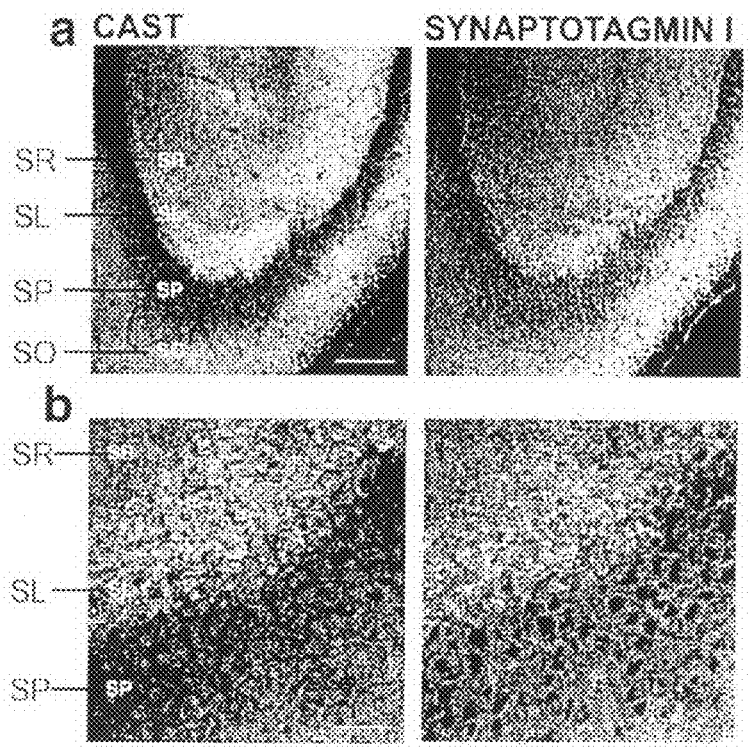
FIG. 4 is a set of photographs showing (A) immunohistostainings of the mouse hippocampal region with anti-CAST antibody and anti-synaptotagmin I antibody; (B) immunohistostainings of a primary culture of rat hippocampal neurons with the anti-CAST antibody, anti-Bassoon antibody, or anti-PS-95 antibody; and (C) immuno-electron micrographs of synapses stained with the anti-CAST antibody.

Mouse hippocampal regions were immunohistostained using anti-CAST antibody, and the presynaptic synaptic vesicle protein, synaptotagmin I, was used as a control. The strongest CAST signal was observed in the CA3 region of the hippocampus (FIG. 4A). This region is referred to as the stratum lucidum and is where synapses are formed between the mossy fiber nerve terminals and the dendrites of pyramidal cells, thus indicating the localization of CAST to synapses.

Figure 4B:
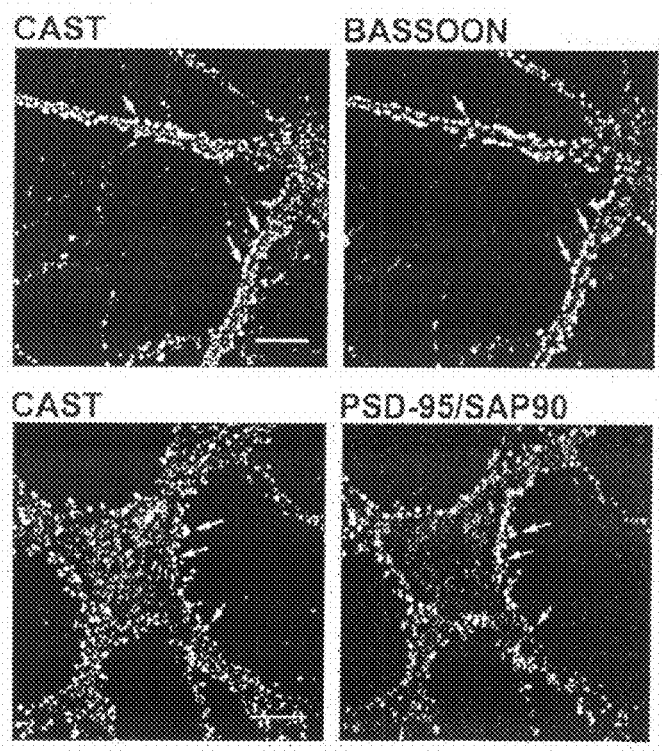

Using a primary culture of neurons from the rat hippocampus, the localization of CAST to synapses was further investigated. On embryonic day 19, hippocampi were excised from rat cerebra and cells were treated with trypsin before being cultured in B-27 medium (Gibco). Cells on the $21^{st}$ day of culture were fixed in 4% paraformaldehyde, treated with 0.2% Triton X-100, co-incubated with the anti-CAST antibody and either the anti-Bassoon antibody or the anti-PS-95 antibody, and then the localization of each protein was detected using a secondary antibody. Images of the synaptic pattern of CAST showed it was expressed together with Bassoon and PS-95 along the dendrite (FIG. 4B), strongly indicating the localization of CAST to synapses.

Figure 4C:
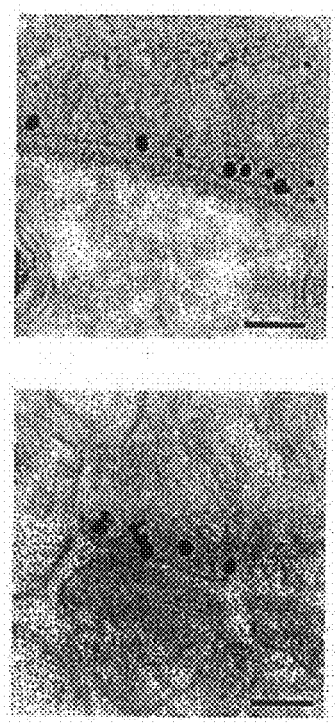

Furthermore, analysis using immunoelectron microscopy revealed that CAST is localized very closely to the presynaptic active zone of the hippocampal CA3 region (FIG. 4C).

Example 5

Identification of the Binding Protein of CAST

Proteins binding to CAST were identified in order to analyze the function of CAST in the active zone.

Immunoprecipitation of the P2 fraction with the anti-CAST antibody saw CAST co-precipitate with active zone proteins, RIM1 and Bassoon (FIG. 5). Bassoon's molecular weight of 4,000,000 or more renders its biochemical analysis problematic, and thus the binding of p120 with RIM1 was further analyzed.

In 1997, RIM1 was isolated as a target protein for small G protein Rab3A; however, its function is still unknown (Wang et al., Nature. 388: 593-598, 1997). Recently reported RIM1 knockout mice revealed that RIM1 plays an extremely important role in synaptic plasticity. However, these reports did not show the initially expected involvement of RIM1 in active zone formation (Castillo P. E. et al., Nature 415:327-330, 2002; Schoch S. et al., Nature 415:321-326, 2002).

When GST fusion proteins of RIM1 and p120 proteins were prepared to determine the mutual binding domains, it was revealed that the PDZ domain of RIM1 and the C-terminus of CAST directly bind to each other (FIG. 6). In particular, the terminal Ile-Trp-Ala (IWA) amino acids were revealed to be essential to this binding. The above-described results indicated that CAST functions as a protein scaffold for RIM1 in the active zone.

Figure 7:
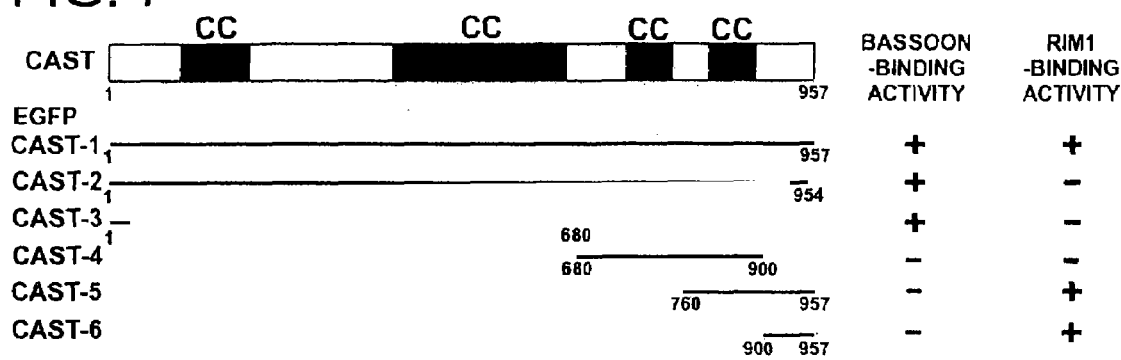
FIG. 7 is a diagram showing the presence or absence of binding activity between whole CAST and RIM1.
Figure 8A:
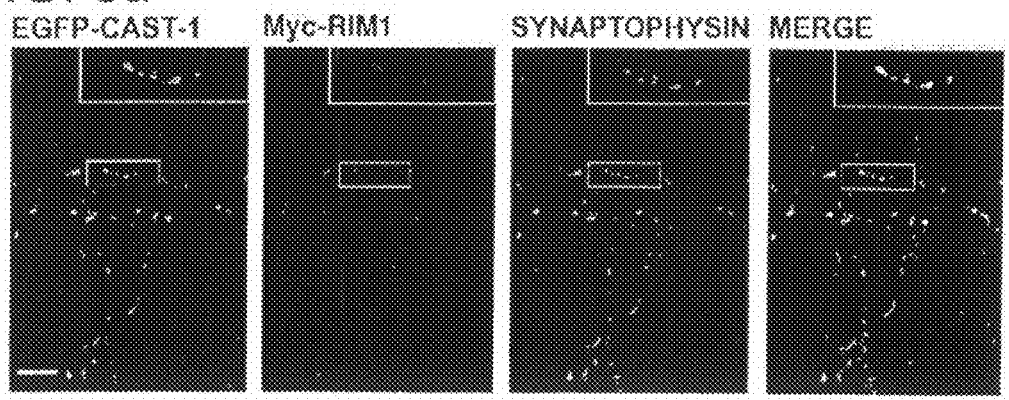
FIG. 8 is a series of photographs showing the distribution of the fusion protein of ECFP and CAST that does not have binding activity with respect to RIM1 (CAST-2). CAST distribution in the synaptic active zone was revealed to be independent of the binding activity with RIM1.
Figure 8B:
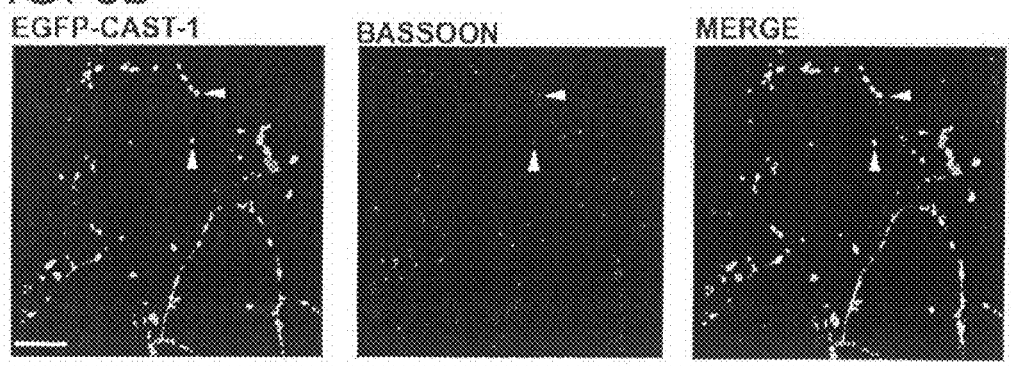
Figure 8C:
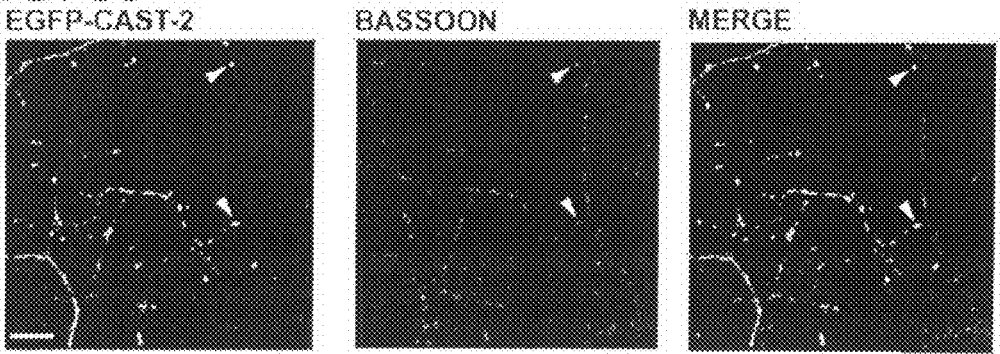
Figure 8D:
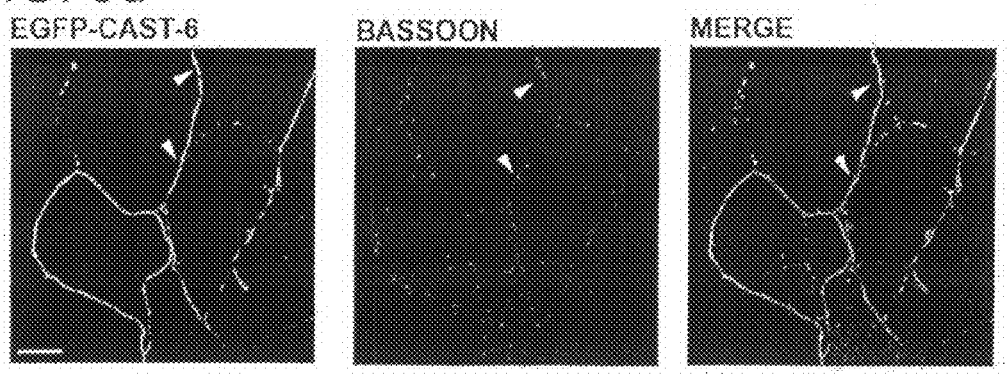

A primary culture of rat hippocampal neurons was then used to examine whether CAST actually functions as a protein scaffold for RIM1 in neurons. When CAST and RIM1 were co-expressed in neurons, they were co-localized with the synaptic marker protein, synaptophysin (FIGS. 7 and 8). When CAST was expressed alone, the same results were obtained. Furthermore, a mutant CAST, in which the C-terminal IWA amino acids necessary for binding RIM1 had been deleted, could also be localized to synapses. Thus it was revealed that RIM1 is not required for the localization of CAST to synapses.

Next, whether CAST is necessary for the localization of RIM1 to synapses was examined. When expressed alone, RIM1 was co-localized with Bassoon to synapses (FIG. 9). However, mutant RIM1, deprived of the PDZ domain necessary for binding to CAST, was not localized to synapses. However, when RIM1 was co-expressed with CAST, both the PDZ domain and CAST were co-localized with Bassoon to synapses. The above-described results proved that RIM1 localizes to the synapses by binding, via its PDZ domain, to the IWA sequence of CAST.

The present inventors found that CAST is a very important active zone protein in determining the localization of RIM1. The formation of a molecular complex based on the interaction between active zone proteins is likely to contribute a great deal to the molecular basis of active zone formation.

Example 6

Involvement of RIM1 Binding to CAST in Neurotransmitter Release

In the next set of experiments, the present inventors examined whether the binding of RIM1 and Bassoon to CAST is involved in neurotransmitter (acetylcholine) release. The present inventors used superior cervical ganglion neurons (SCGNs) in culture for this purpose, because i) peptides or proteins can be readily introduced into the relatively large presynaptic cell bodies using microinjection, ii) the injected materials can rapidly diffuse to nerve terminals forming synapses with adjacent neurons, and iii) the effects of the stimulated release of acetylcholine can be accurately monitored by recording the excitatory postsynaptic potentials (EPSPs) evoked by action potentials in the presynaptic neurons (Mochida S. et al., Proc Natl Acad Sci USA. 95 (24):14523-8, 1998).

The present inventors first prepared the RIM-interacting domain (RID) peptide, and the RIDΔIWA and scrambled RID peptides as controls (FIG. 10a). The last three amino acids (IWA) are critical for the binding of RIM1 to CAST (Ohtsuka T. et al., J Cell Biol. 158 (3):577-90, 2002). In vitro binding assays revealed that RID, but not RIDΔIWA or scrambled RID, inhibited the binding of RIM1 to CAST (FIG. 10b).

The present inventors next microinjected these peptides into presynaptic SCGNs. RID inhibited synaptic transmission (FIG. 10c and FIG. 10d). At 70 minutes after RID injection, EPSP amplitude was reduced by −33+9.1% (n=5). In contrast, neither RIDΔIWA nor scrambled RID produced a significant decrease in EPSP amplitude (p=0.025, 0.023 unpaired t-test at 70 minutes after the injection of RID versus RIDΔIWA, and RID versus scrambled RID, respectively).

These results indicate that CAST dynamically binds RIM1 and that this dynamic binding is necessary for neurotransmitter release. It has been shown that the direct binding of RIM1 and Munc13-1 is involved in the priming of synaptic vesicles (Betz A. et al., Neuron. 30 (1): 183-96, 2001) and that the localization of RIM1 at the CAZ appears to be CAST-dependent (Ohtsuka T. et al., J Cell Biol. 158 (3):577-90, 2002). The inhibition of RIM1 binding to CAST may affect the RIM1-Munc13-1 pathway, presumably by mislocalization of RIM1 at the active zone, resulting in reduction of neurotransmitter release.

What is claimed is:

1. A method of screening for a substance that specifically binds with an isolated protein selected from the group consisting of:
   (a) an isolated protein having the amino acid sequence set forth in SEQ ID NO: 2;
   (b) an isolated protein which binds to Rab3A-interacting molecule (RIM1), wherein said protein
      (i) has an amino acid sequence with one to nine amino acid deletions, substitutions, or additions in the amino acid sequence of SEQ ID NO: 2; and
      (ii) contains Ile-Trp-Ala at the C-terminus;
   (c) an isolated protein encoded by an isolated DNA that hybridizes under stringent conditions to a DNA that has a nucleotide sequence complementary to the nucleotide sequence set forth in SEQ ID NO: 1, wherein the stringent conditions are hybridization at 65° C. for two and a half hours followed by washing in 2×SSC and 0.05% SDS at 25° C. for five minutes; and
   (d) an isolated protein encoded by an isolated DNA having a nucleotide sequence with 95% or more homology to the nucleotide sequence set forth in SEQ ID NO: 1 and encoding a protein which binds to RIM1, and wherein said protein contains Ile-Trp-Ala at the C-terminus;

said method comprising
   (1) contacting a test substance with said protein; and
   (2) detecting the presence of binding between the test substance and said protein.

2. The method of claim 1, wherein said protein is produced by:
   (1) culturing a host cell comprising an isolated DNA selected from the group consisting of:
      (a) a DNA encoding a protein having the amino acid sequence set forth in SEQ ID NO: 2; and
      (b) a DNA encoding a protein which binds to RIM1, wherein said protein
         (i) has an amino acid sequence with one to nine amino acid deletions, substitutions, or additions in the amino acid sequence of SEQ ID NO: 2; and
         (ii) contains Ile-Trp-Ala at the C-terminus;
      (c) an isolated DNA encoding a protein having the amino acid sequence set forth in SEQ ID NO: 2 and having nucleotides 59 to 2929 of the nucleotide sequence set forth in SEQ ID NO: 1;
      (d) an isolated DNA that hybridizes under stringent conditions to a DNA that has a nucleotide sequence complementary to the nucleotide sequence set forth in SEQ ID NO: 1, wherein the stringent conditions are hybridization at 65° C. for two and a half hours followed by washing in 2×SSC and 0.05% SDS at 25° C. for five minutes;

(e) an isolated DNA having a nucleotide sequence with 95% or more homology to the nucleotide sequence set forth in SEQ ID NO: 1 and encoding a protein which binds to RIM1, and wherein said protein contains Ile-Trp-Ala at the C-terminus; and (f) an isolated DNA encoding a protein having the amino acid sequence set forth in SEQ ID NO: 2 and having the nucleotide sequence set forth in SEQ ID NO: 1; and (2) collecting the protein from the culture.

* * * * *